US006301380B1

United States Patent
Mullins et al.

(10) Patent No.: US 6,301,380 B1
(45) Date of Patent: *Oct. 9, 2001

(54) FOLD INSPECTION DEVICE FOR TRANSPARENT OVERWRAP FILM

(75) Inventors: Michael J. Mullins, Chesterfield; Barry S. Smith, Hopewell, both of VA (US)

(73) Assignee: Philip Morris Incorporated, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/928,161

(22) Filed: Sep. 12, 1997

(51) Int. Cl.[7] ............................................. G06K 9/00
(52) U.S. Cl. .................... 382/141; 348/127; 250/372; 209/587
(58) Field of Search ................................ 382/141, 143; 209/536, 578, 587, 617, 509; 356/240.1, 239.4; 700/95–212; 348/86, 125, 127, 128, 131; 250/372

(56) References Cited

U.S. PATENT DOCUMENTS

| 4,053,056 | * | 10/1977 | Day ........................... 209/587 |
| 4,520,388 | * | 5/1985 | Kellie ........................ 348/128 |
| 4,865,447 | * | 9/1989 | Shay ......................... 356/239.4 |
| 4,972,494 | * | 11/1990 | White et al. ................ 382/143 |
| 4,976,544 | | 12/1990 | Neri . |
| 5,013,905 | | 5/1991 | Neri . |
| 5,235,649 | | 8/1993 | Reda . |
| 5,264,700 | * | 11/1993 | Tommasini et al. ......... 250/372 |
| 5,366,096 | | 11/1994 | Miller . |
| 5,414,270 | | 5/1995 | Henderson et al. . |
| 5,448,365 | | 9/1995 | Grollimund et al. . |
| 5,515,159 | * | 5/1996 | Sites et al. .................. 348/131 |
| 5,537,670 | | 7/1996 | Cox et al. . |

OTHER PUBLICATIONS

"Shed Some Light on Bulb Selection", The Home Spot, http://www.homespot.com/maines.*

* cited by examiner

Primary Examiner—Samir Ahmed
(74) Attorney, Agent, or Firm—Clinton H. Hallman, Jr.; Kevin B. Osborne; Charles E. B. Glenn

(57) ABSTRACT

An imaging apparatus and process for inspecting polymeric film seals and folds. Incident light is applied to the package to cause either reflected or transmitted light to reflect a pass through the poly wrap. The wrap affects the transmitted or reflected image in a manner which can be analyzed to determine the quality of the poly film application.

18 Claims, 11 Drawing Sheets

FOLD INSPECTION DEVICE FOR TRANSPARENT OVERWRAP FILM

I. BACKGROUND OF THE INVENTION

A. Field of the Invention

This invention relates to inspection systems for overwrap on packaged goods to ensure a complete and quality overwrap, proper graphics, and pack construction.

B. Description of the Prior Art

Inspection systems for packaged goods generally are known for use as quality control devices, and process control for manufacturing. Consumers may outright reject or return defectively packaged merchandise, for a variety of reasons. Improperly sealed consumer goods can raise safety and freshness concerns and perfectly good items will routinely be returned for refund and disposal with concomitant losses. Inspection is one way of ensuring a minimum of packaging defects.

High speed inspection systems have limited time to determine the acceptability of a product and are generally limited to examination of planar surface features; e.g. a misprint or a defect in the product exterior. Objects with a circular cross section; e.g. cigarettes, can be scanned sequentially using image scanning technology such as that in U.S. Pat. Nos. 5,235,649, 5,366,096, 5,414,270, 5,013,905, and 4,976,544, which are incorporated herein in their entireties.

However, a transparent or partially transparent wrapper; e.g. a poly film wrapper, is invisible to normal optical inspection devices. A method for inspecting the condition of the wrap is needed to ensure the packaging is intact and defective goods are not shipped.

C. Summary of the Invention

Applicants have developed a novel imaging process to inspect polymeric film seals and folds. Incident light is applied to the package to cause either reflected or transmitted light to reflect a pass through the poly wrap. The wrap will affect the transmitted or reflected image in a manner which can be analyzed to determine the quality of the poly film application.

II. BRIEF DESCRIPTION OF THE FIGURES

III. DETAILED DESCRIPTION

Exemplary arrangements of the invention may now be seen by reference to the figures and this description. These examples are meant to serve as illustrations of the invention, and as such should not be construed as limiting the invention.

The present inventive vision system is used to enhance product quality, but additionally is utilizable as a process inspection/control system. It allows an operator to see the manufacturing process dynamically as the cigarettes are being packaged. Therefore, a case of defectively packaged work is not packaged up and sent to inventory, to be discovered in a later quality audit, or worse, by a consumer. Thus, such a system is preferentially used in mainstream packaging.

Figure 1:
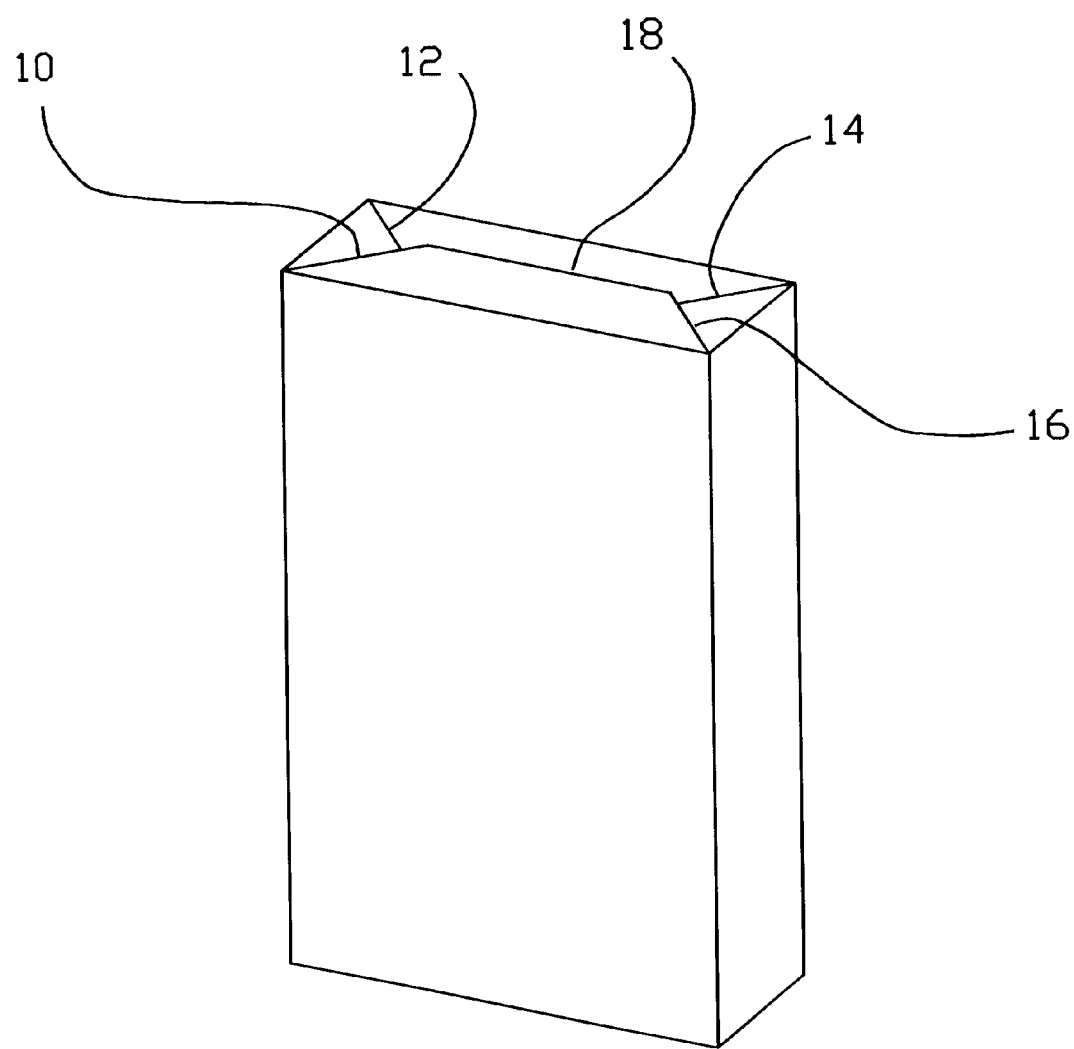
FIG. 1 is a perspective view of a package wrapped in poly film.
Figure 2:
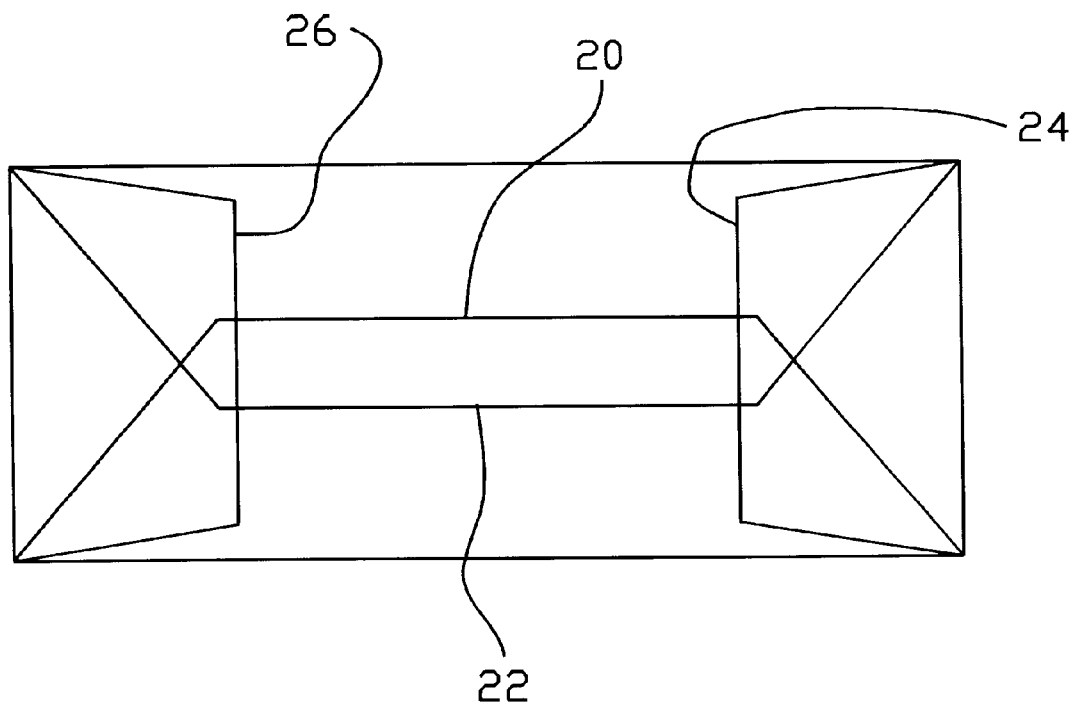
FIG. 2 is an end view of a package wrapped in poly film.

Turning now to FIG. 1, an example of a packaged item is seen. The "ideal" wrap would have a total of 5 lines, i.e. lines 10, 12, 14, 16, and 18 as closure seams, with no overlap, or minimal overlap. FIG. 2 illustrates the closure in an end view of the package of FIG. 1. The wrap system of FIG. 2 illustrates that the excess wrap may be easily folded over the cut to make a heat sealed or glued closure.

Lines 20, 22, 24, and 26 all originated with the same (upper or lower) edge of the poly film wrap. In a manner similar to wrapping any package, the excess film is physically folded over from side-to-side, then end-to-end, or vice versa. Sealing means, usually a heat treatment or the application of an adhesive substance, completes the wrapping procedure.

A properly wrapped package, depending on the sequence of folds, the placement of the overwrap, and amount of excess material, will have a distinctive "fold" pattern such as may be seen in FIG. 2.

Figure 5:
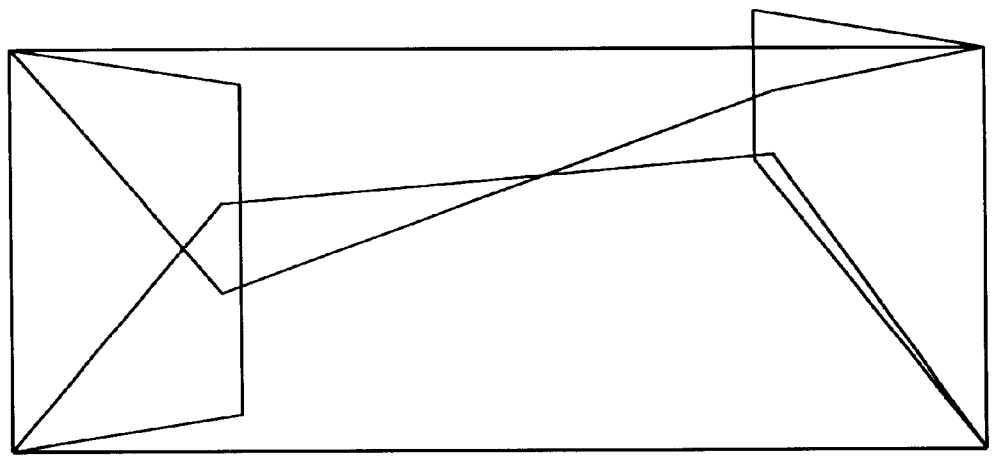
FIG. 5 is an end view of a defectively wrapped package.

An error in folding, placement of overwrap, or a tear in the wrap will drastically affect the pattern on the end. For example, in FIG. 5, the entire wrap is skewed to one side and the pattern is clearly visible as "wrong."

Poly film, usually, is invisible when used as an overwrap—allowing advertising indicia or package printing to show through. Thus, standard inspection techniques will fail to pick up the overwrap defects, be they misplacement, misfolding, tearing, wrinkling, or other defects.

Applicants novel system takes advantage of a unique property of clear or partially clear poly film. The film acts, for brief distances, as a light conductor. In many ways this is similar to fiber optic light transmission, when an endpoint is reached with a medium which has a different index of refraction, light appears to emanate from the endpoint, causing it to "glow."

Figure 4:
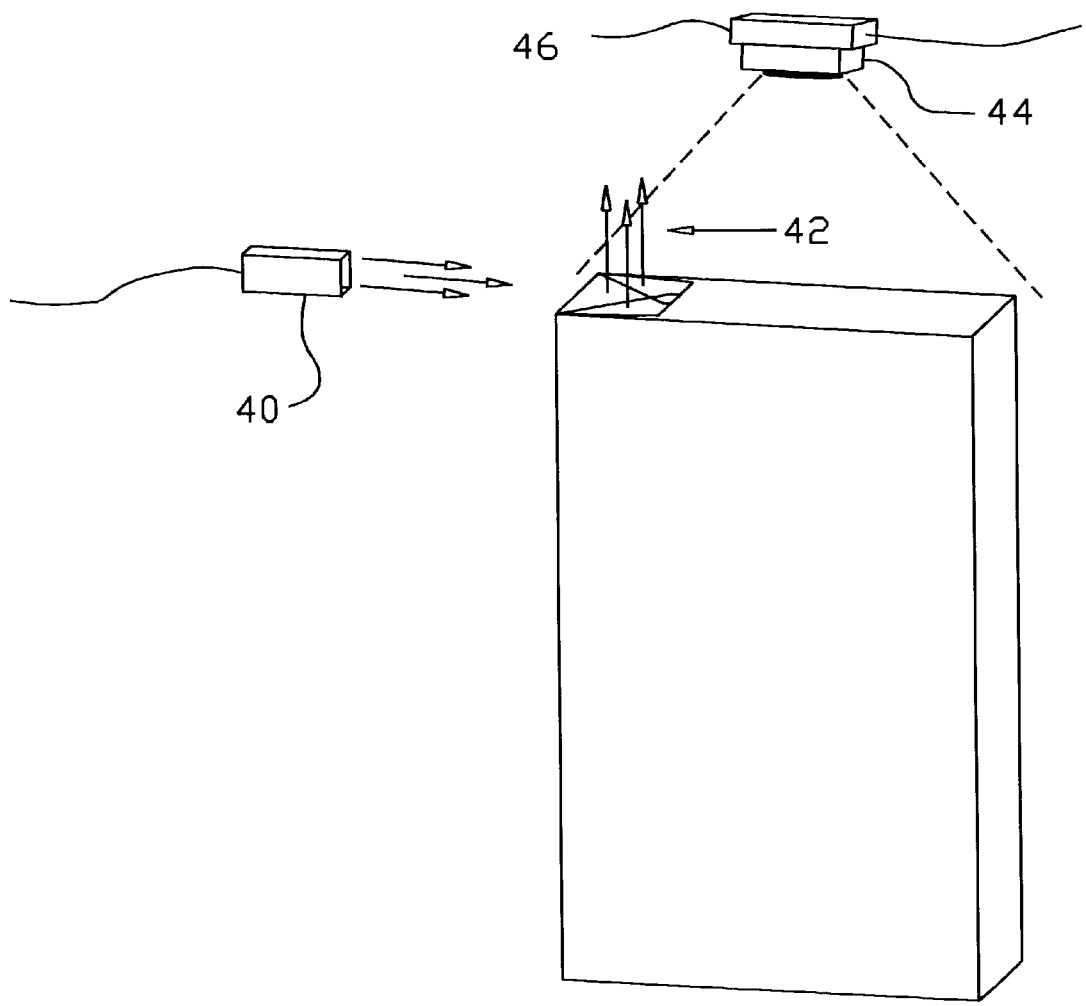
FIG. 4 is a schematic view of an inspection system according to the present invention.

Thus, as may be seen in FIG. 4, light source 40 sends incident light into the wrap itself. The light "escapes" from the poly film wrap at edges and folds where it reaches a reflective boundary. The escaped light 42 is captured via lens 44 to camera 46 and is thence sent to an image processor (not shown).

Figure 6:
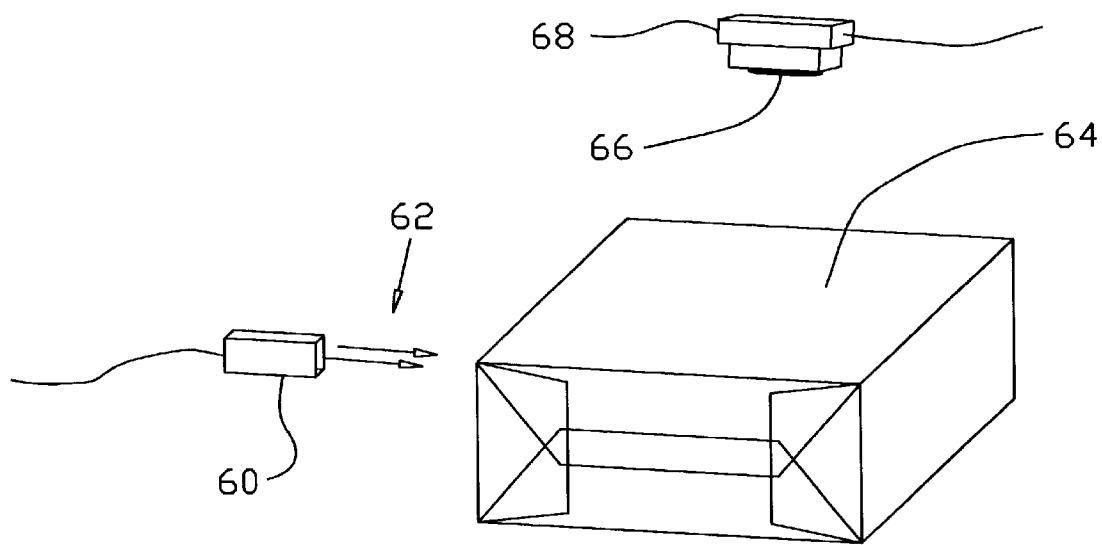
FIG. 6 is a perspective view of an exemplary preferred system for detecting defects in planar surfaces.

Image processing is undertaken to yield an image of the folds, or a clear surface image. In one embodiment, the surfaces without folds may be imaged for defects. By way of example, FIG. 6 illustrates such a system. Incident light generator 60 generates incident light 62 which is projected into poly film 64. Strong reflected or diverted light will be picked up at lens 66 and focused on camera 68 for transmission to image analysis software.

Figure 7:
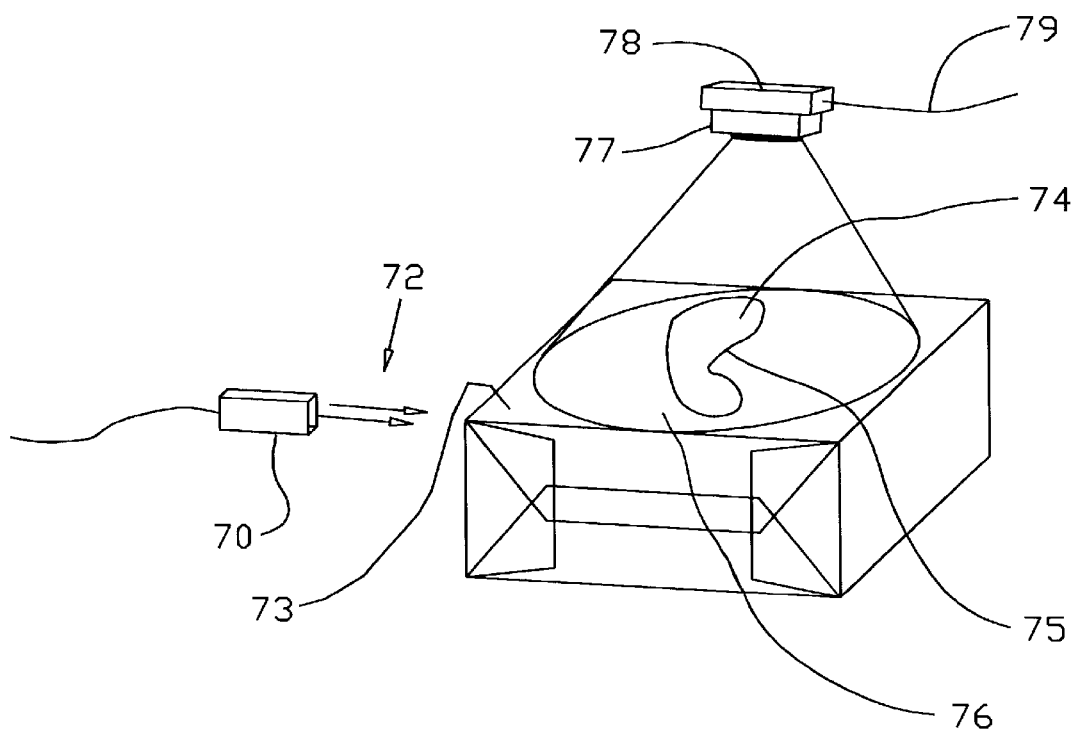
FIG. 7 is the system of FIG. 6 with a defect present.
Figure 8:
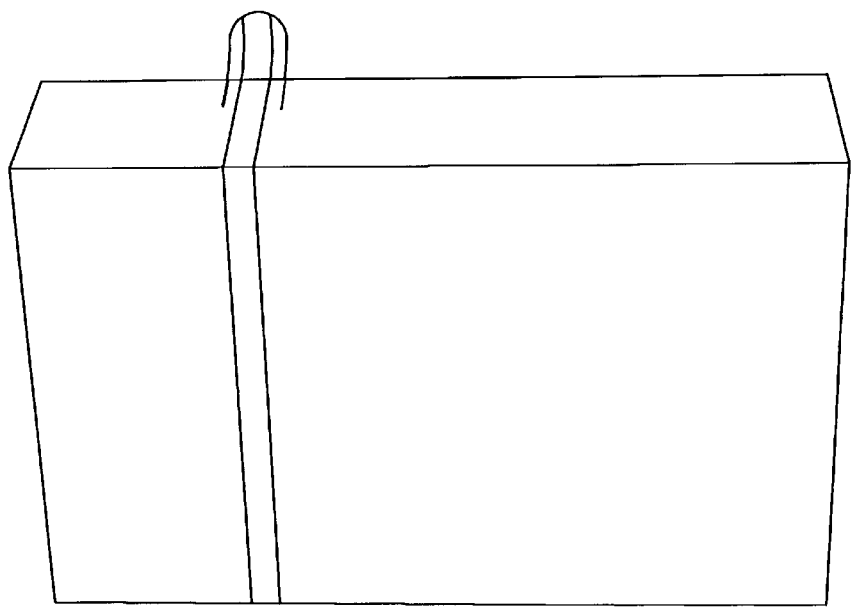
FIG. 8 is a perspective view of a package with a tear tape in the poly film.
Figure 9:
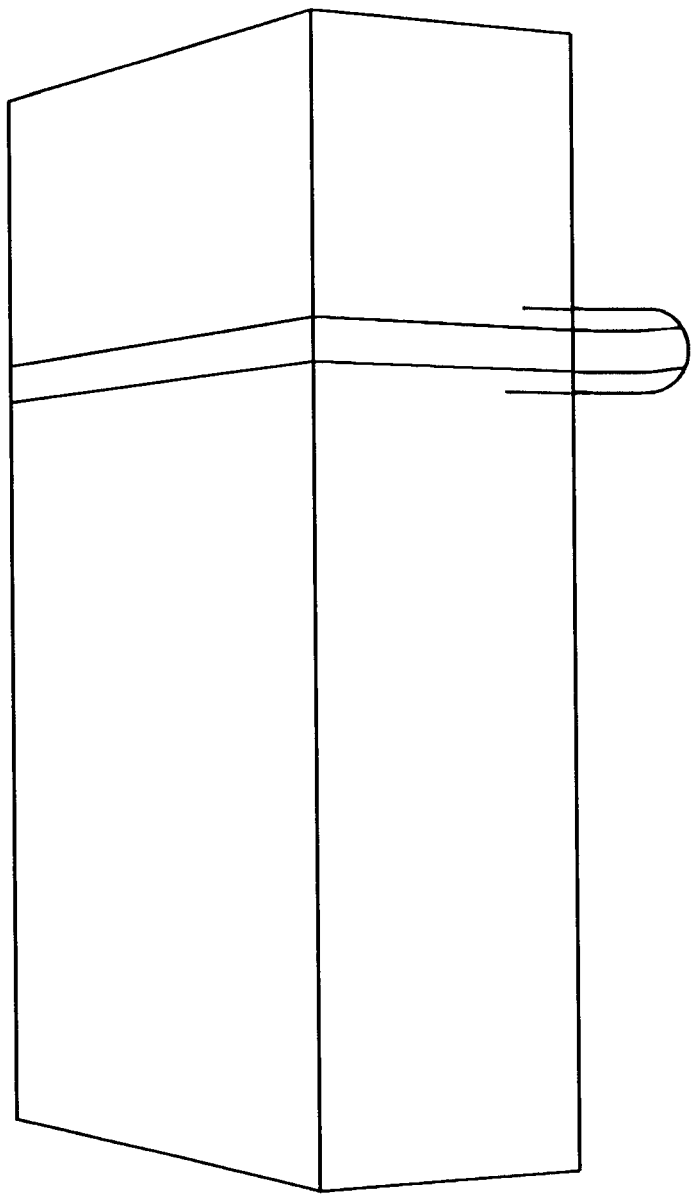
FIG. 9 is a perspective view of a package with a tear tape in the poly film.
Figure 10:
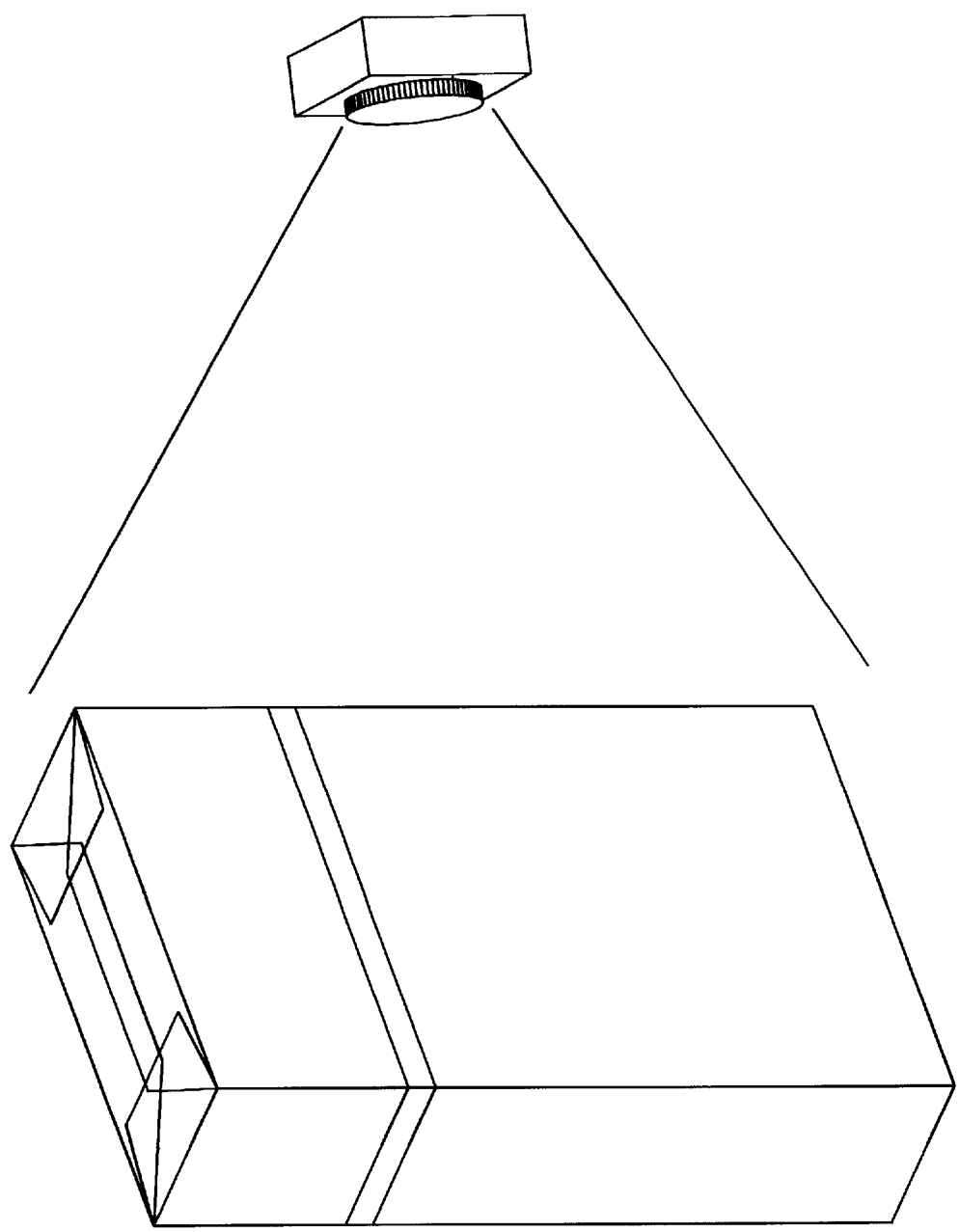
FIG. 10 is a perspective view of an inspection system according to the present invention.
Figure 11:
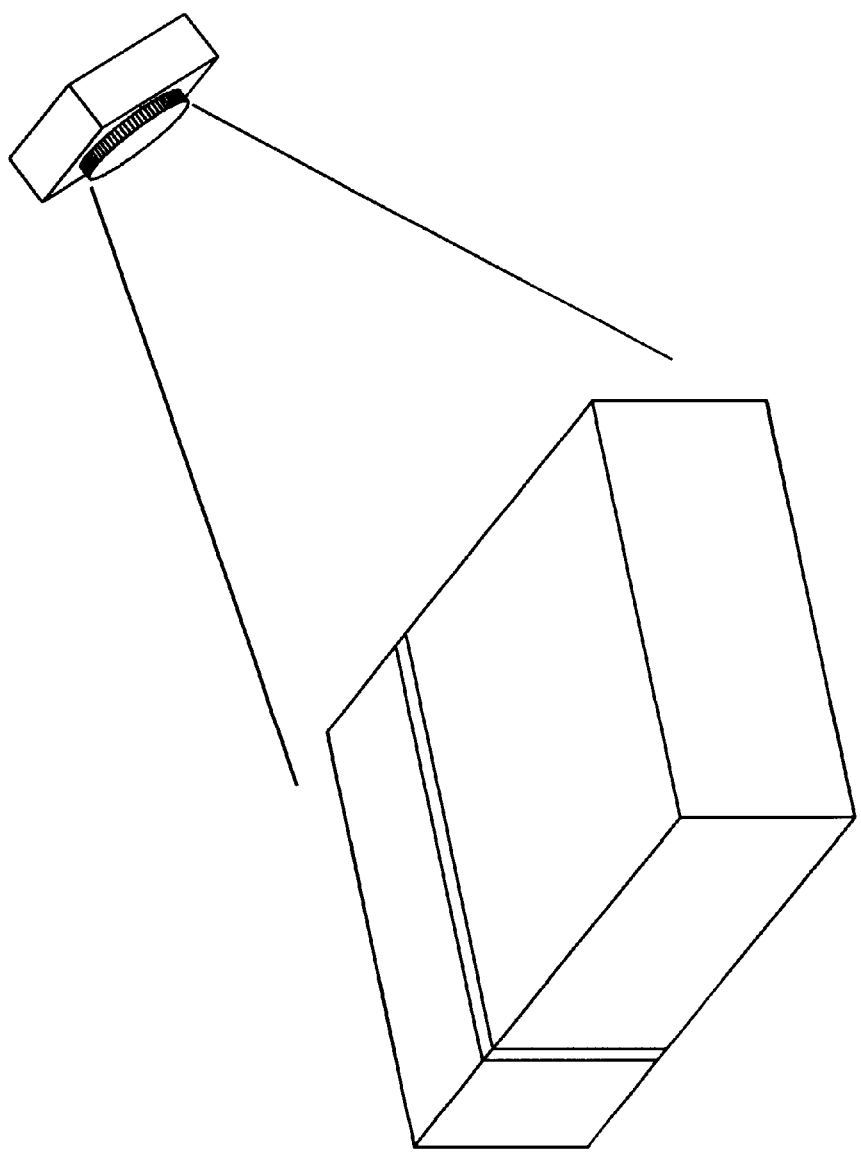
FIG. 11 is a perspective view of an inspection system according to the present invention.

FIG. 7 illustrates a defect being detected by the novel system. Light source 70 generates incident light 72 which enters the poly film surface 73. Defect 74 represents a missing portion of poly film wrap. The edges of the defect 75 are clearly illuminated by the light in the poly film. The defect is within field of vision 76 of camera 78 and lens 77. The image, including defect, is transmitted via cable or data transfer device 79 to be processed.

The image analysis of the present invention is performed by the following steps The fold pattern or tear pattern is captured in the camera scan. Color or black & white scanning may be used, but black and white scanning is faster, has a higher resolution, and is more easily adapted for partial scanning. The image is transferred via I/O circuitry or the like to the computer. The computer has reference images stored which are recognized as acceptable images. U.S. Pat. No. 5,537,670 provides a thorough explanation of such a system and is incorporated herein by reference.

A package such as that seen in FIG. 7, with its flaw in the surface, would be compared against a databank of acceptable reference images, then rejected.

Figure 3:
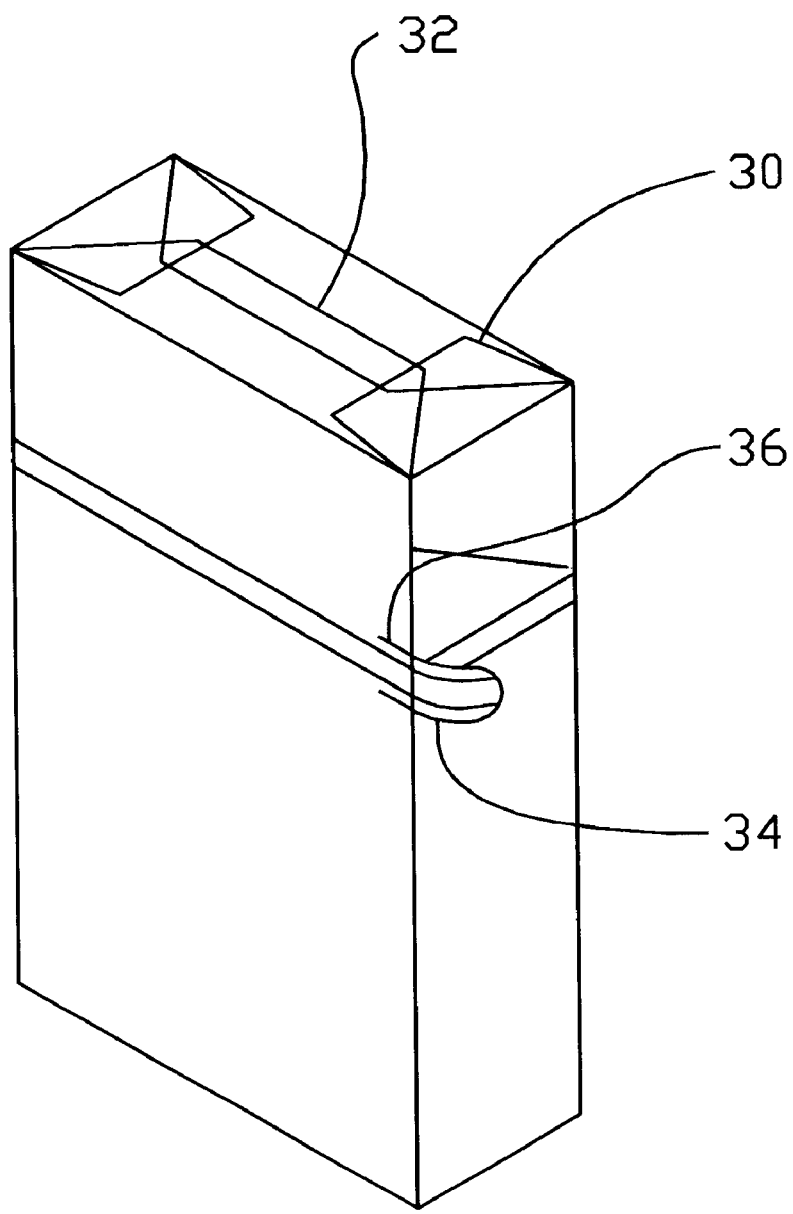
FIG. 3 is a perspective view of a package with a tear tape in the poly film.

The system also may inspect for tear tape cuts and proper tear tape placement, as may be seen in FIG. 3.

While edges 32 and folds 30 may be inspected, so too may be tear tape protrusion 34 and tear tape cuts 36, for placement and cutting completeness.

The inspection system may also take advantage of the blocking characteristics of a poly wrap film which has printing upon it. The image printed upon the film will act to block light transmission in a particular pattern, or reduce it. The system can rapidly "learn" this light scattering by allowing it to store acceptable images in its database. Then, occluded light patterns are learned as acceptable. Other wrap patterns likewise may be learned in a manner similar to the system's initial programming with conventional packaging fold and surface images.

Camera devices may be standard video cameras, charge-coupled-devices, or other optical detectors which may receive transmitted or reflected light from the poly film.

The light source utilized may be fluorescent, incandescent, solid state generated (e.g. LED constant or "pulsed"), infrared, or other type of light, so long as the wavelength will be transmitted by the poly film. An exemplary strobe is manufactured by EG&G, Inc. of Salem, Mass. Part number 2020 is particularly useful.

An apparatus according to the present invention will be useful for the optical inspection of objects wrapped in a transparent or semi-transparent material.

The transparent material is a filmic material, laminated or unlaminated, coated or uncoated, with or without an image on the film. The film is made from polypropylene, polyethylene, cellophane, or the like. Thickness may be in the range of from about 0.1 mil to 10 mils, preferably from the range of 0.5 to 3 mils, more preferably from about 1–2 mils, most preferably about 1.5 mils.

The apparatus will have a light source positioned such that light enters the transparent wrap material at an intensity greater than ambient light conditions, and an optical detector which receives light from the transparent wrap material. A light source from 1 to 100 watts may be used, but it has been found most efficient to occlude the ambient light to some extent and use lights in the lower end of that range, from 1–25 watts, and preferably from 1–15 watts output.

The apparatus will further be equipped with an image analyzer which receives input from the optical detector and determines the acceptability of that input.

Panasonic™'s GPMF702D black & white camera is particularly useful and is commercially available for use as the optical detector. Such a camera is capable of partial scanning which results in increased frame speed and higher inspection rates, and is easily networked into a 486 computer by a conventional means.

The presently preferred controller is a 486 Pentium™ based processing unit, manufactured and designed by PPT of Eden Prairie, Minn. under the designation VPC 400 Vision Processing Controller. The controller preferably is linked to an optical image display which can display the images generated visually to an operator who can adjust or halt a packaging machine manually. An automated feedback loop may also be provided for correcting certain known defects, e.g. from a library of "defective" images, certain pre-programmed corrective steps may be automatically executed by the controller and inputted into the packaging machine.

One of skill in the art, having regard for this disclosure, may make many modifications and improvements hereto without departing from the scope of the appended claims.

Having described the invention as above, we claim:

1. An apparatus for the optical inspection of transparent or semi-transparent material surrounding and wrapped around an object, at least a portion of said transparent or semi transparent material being folded so as to create a pattern of at least one fold comprising:

a light source positioned such that light enters the transparent or semi-transparent material at an intensity greater than ambient light conditions, is conducted therealong until it reaches at least one fold, and emanates at said fold;

an optical detector which is positioned to receive the light which emanates from the at least one fold of the transparent wrap material; and an image analyzer which receives input from the optical detector and determines the acceptability of that input by comparing the input to a set of stored fold patterns.

2. An apparatus as claimed in claim 1, wherein the light source is positioned at an angle of the object to be inspected.

3. An apparatus as claimed in claim 1, wherein the light source is incandescent or fluorescent.

4. An apparatus as claimed in claim 1, wherein the light source is ultraviolet.

5. An apparatus as claimed in claim 1, wherein the light source is infrared.

6. An apparatus as claimed in claim 1, wherein the light source is in the visible wavelength.

7. An apparatus as claimed in claim 1, wherein the optical detector is a camera.

8. An apparatus as claimed in claim 7, wherein the camera is a charge-coupled device.

9. An apparatus as claimed in claim 7, wherein the camera is sensitive to infrared or ultraviolet spectra.

10. An apparatus as claimed in claim 7, wherein the camera is a scanning black and white camera.

11. An apparatus as claimed in claim 7, wherein the camera is a partial field scanning camera.

12. An apparatus as claimed in claim 1, wherein the light source is solid state.

13. An apparatus as claimed in claim 12, wherein the light source comprises at least one light emitting diode.

14. An apparatus as claimed in claim 1, wherein the light source is constant.

15. An apparatus as claimed in claim 12, wherein the light source is pulsed or strobed.

16. A method for optically inspecting a transparent or semi-transparent wrapper surrounding and wrapped around a package, at least a portion of said transparent or semi transparent wrapper being folded so as to create a pattern of at least one fold comprising the steps of:

providing a wrapped article to be inspected;

directing incident light upon the article such that at least some of the incident light enters the wrapper and is conducted therealong;

detecting the light escaping from the wrapper from the at least one fold;

examining the pattern of escaped light from the at least one fold and comparing it to known patterns of light from folds; and determining the acceptability of the wrapped article by comparing the pattern of escaped light to a database of known images of patterns of escaped light from acceptable packages.

17. An apparatus for the optical inspection of a transparent or semi-transparent polymeric filmic wrap material surrounding a cigarette package at least a portion of said wrap material being folded so as to create a pattern having at least one fold comprising:

a strobed light source positioned such that light enters the wrap material at an intensity greater than ambient light conditions, is conducted by the wrap material for a distance, and exits the wrap material at the at least one fold;

a partial field scanning black and white optical detector which receives the light which exits from the at least one fold of the transparent wrap material; and an image analyzer which receives input from the optical detector and determines the acceptability of that input by comparing the input to a database of known patterns.

18. An apparatus as claimed in claim 1, further comprising an optical display.

* * * * *